United States Patent [19]

Taylor et al.

[11] Patent Number: 5,234,570
[45] Date of Patent: Aug. 10, 1993

[54] REFERENCE ELECTRODE WITH ANNULAR JUNCTION

[75] Inventors: Dale F. Taylor; William H. Stoddard, Jr., both of Schenectady, N.Y.

[73] Assignee: General Electric Company, Schenectady, N.Y.

[21] Appl. No.: 754,487

[22] Filed: Sep. 3, 1991

[51] Int. Cl.[5] .......................................... G01N 27/30
[52] U.S. Cl. ..................................... 204/435; 204/400
[58] Field of Search ..................... 204/400, 435, 153.21

[56] References Cited

U.S. PATENT DOCUMENTS

| | | | |
|---|---|---|---|
| 4,495,052 | 1/1985 | Brezinski | 204/435 |
| 4,500,413 | 2/1985 | Taylor et al. | 204/435 |
| 4,576,667 | 3/1986 | Taylor et al. | 156/89 |
| 4,948,492 | 8/1990 | Niedrach et al. | 204/435 |
| 5,034,113 | 7/1991 | Iwamoto | 204/435 |

Primary Examiner—John Niebling
Assistant Examiner—William T. Leader
Attorney, Agent, or Firm—James E. McGinness; James Magee, Jr.

[57] ABSTRACT

A reference electrode is disclosed, comprised of a ceramic housing comprised of a bottom and a sidewall means extending from the bottom to a cylindrical housing top to define an inner channel. The channel contains a silver electrode extending therefrom and a deposit of a silver salt. The housing having a bore substantially radial to the axis of the housing extending through oppositely facing sidewall means, and a ceramic rod configured to fit in the bore and form a friction bond is positioned in the bore to form an annular junction that permits transfer of ions across the junction. Means for electrically isolating the silver electrode are mounted on the housing top.

2 Claims, 1 Drawing Sheet

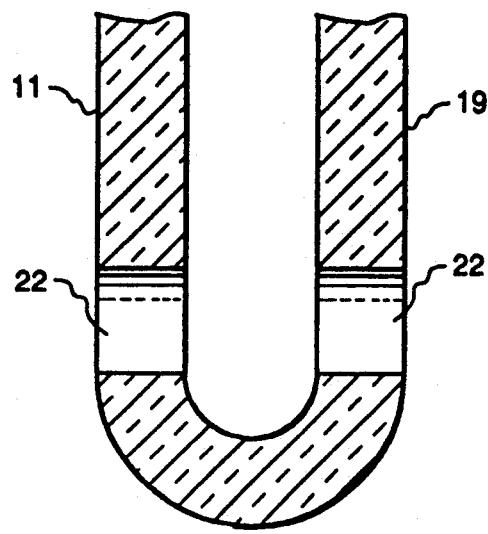
FIG. 2
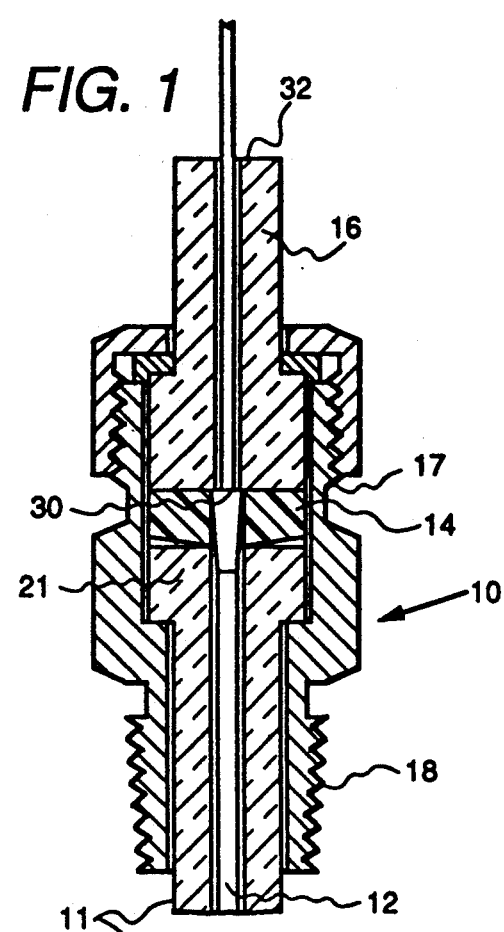
FIG. 1
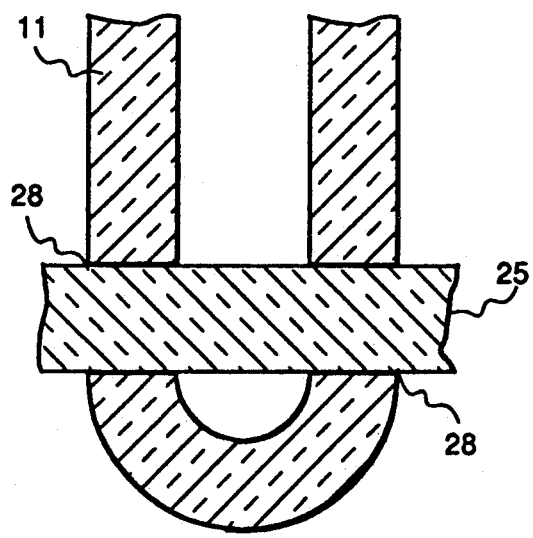
FIG. 3
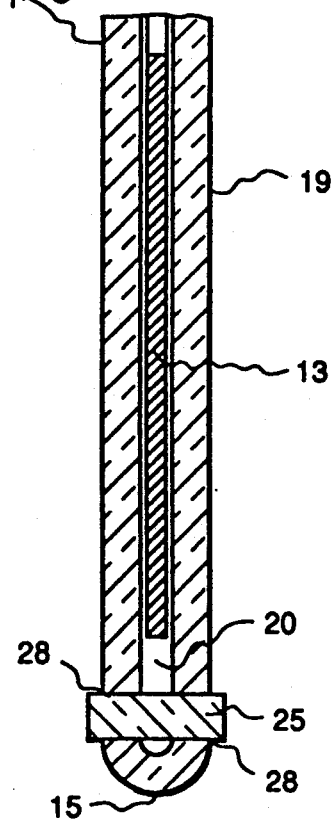

REFERENCE ELECTRODE WITH ANNULAR JUNCTION

BACKGROUND OF THE INVENTION

This invention is concerned with reference electrodes having ceramic housings suitable for use in a high-pressure, high-temperature environment.

Reference electrodes having a ceramic housing, such as stabilized zirconia, are disclosed in U.S. Pat. Nos. 4,500,413, and 4,576,677, incorporated herein by reference. Such electrodes are suitable for use in high-pressure, high-temperature environments. Improved stability in the reference potential is provided by an annular liquid junction between the electrolyte within the electrode, and the liquid the electrode is immersed in. In the '413 and '677 patents a closely fitting ceramic plug is sintered in a hole in the ceramic housing of the electrode to form a porous bond therebetween. The porous bond forms the annular junction that provides for diffusion of ionic species into or out of the electrode, and for escape of the electrolyte when volume increases due to thermal expansion from rapid heating. The liquid junction also provides limited fluid transfer from the electrolyte to maintain chemical equilibrium and a stable concentration of ions in the electrolyte.

It is an object of this invention to provide a reference electrode suitable for use in high-temperature, high-pressure environments, having an annular liquid junction formed from a friction fitting.

BRIEF DESCRIPTION OF THE INVENTION

A reference electrode is comprised of a ceramic housing comprised of a bottom and a sidewall means extending from the bottom to a cylindrical housing top to define an inner channel. The channel contains a silver electrode extending therefrom and a deposit of a silver salt. The housing having a bore substantially radial to the axis of the housing extending through oppositely facing sidewall means, and a ceramic rod configured to fit in the bore and form a friction bond is positioned in the bore to form an annular junction that permits transfer of ions across the junction. Means for electrically isolating the silver electrode are mounted on the housing top.

BRIEF DESCRIPTION OF THE DRAWINGS

FIG. 1 is a side view in cross section of a reference electrode having an annular junction in the electrode housing.

FIG. 2 is an enlarged view showing a bore at the end of the electrode housing in FIG. 1.

FIG. 3 is an enlarged view showing the annular junction at the end of the electrode housing in FIG. 1.

DETAILED DESCRIPTION OF THE INVENTION

The reference electrode of this invention is suitable for use in measurements in high-temperature, high-pressure aqueous environments, for example, found in the recirculation piping of a nuclear reactor. Tests of a reference electrode configuration as shown in FIG. 1 have shown that the reference electrode operates in both static and flowing high-purity water at temperatures and pressures up to at least 290° C. and 1500 pounds per square inch, and in high-purity water injected with hydrogen. It is desirable to minimize hydrogen permeation into the electrode since hydrogen reduces silver ions in the electrolyte within the electrode, and increases the destabilization of the reference potential.

The electrode of this invention finds preferable employment as a reference component of an electrode system involving a metal-metal ion couple and thus the instant electrode can conveniently be a metal insoluble salt-anion electrode, for example, silver salts such as silver bromide, silver iodide, and preferably silver chloride. For the embodiment shown, the device is a silver-silver chloride reference which functions reversibly. Such electrodes consist of a silver metal electrode immersed in a solution containing silver and chloride ions, usually with a source of silver chloride in the solution to fix the activity of the electrolyte. The electrode reaction is:

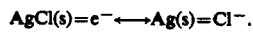

$$AgCl(s) = e^- \longleftrightarrow Ag(s) = Cl^-.$$

For a more detailed discussion in connection with the above, reference is made to "Physical Chemistry" by G. W. Castellan, Chapter 17, "Equilibria in Electrochemical Cells", pp. 344–382, Addision-Wesley Publishing Co., Reading, Mass. (1964), incorporated herein by reference. The use of a reference electrode employing a glass housing for the measurement of pH is illustrated in U.S. Pat. No. 4,264,424, incorporated herein by reference.

Referring to FIG. 1, the reference electrode 10 comprises a tubular housing 11 of a ceramic resistant to high-temperature, high-pressure water, and is resistant to permeation by hydrogen. For example, suitable ceramic materials for housing 11 are zirconia, yttria stabilized zirconia, high purity alumina, sapphire, or ruby. Sapphire, a single crystalline form of alumina, not only provides a requisite electrical insulation but also, by virtue of its single crystalline structure, is highly resistant to attack by water within which it is immersed. Thus, there is no intergranular penetration into the material, even though there will be some general corrosion attack. Suitable yttria stabilized zirconia tubes having an outer diameter of about 0.312 inch, an inner diameter of about 0.188 inch, and a length of about 10 inches for forming housing 11 can be obtained from Coors Porcelain Company, Co.

Housing 11 has a bottom 15, and sidewall means 19 extending therefrom to a cylindrical top 21 to form an inner channel 20. An electrode 12 is suspended in channel 20, and extends beyond the channel above the housing top 21. Electrode 12 is formed from high purity silver with the lower end thereof, shown darkened, coated with silver chloride 13. Preferably, the length of electrode 12 extending within channel 20 is coated with the silver chloride. Electrode 12 is machined to have a step 30 that is greater in diameter than channel 32 in ceramic member 16. When electrode 10 is immersed in a high-pressure aqueous environment, the liquid fills channel 20 and exerts a force on electrode 12. Step 30 prevents the force exerted on electrode 12 from forcing the electrode out of the reference electrode 10.

Sealing member 14, formed of polytetrafluoroethylene containing about 40 weight percent zirconia in order to reduce expansion and distortion at high-temperatures, is positioned between the top 21 of ceramic housing 11 and ceramic member 16. Electrical isolation of electrode 12 is completed with the biasing of sealing member 14 into sealing engagement with ceramic member 16 and housing 11 by the application of pressure thereto by threaded fitting 17. Threaded connection 18 accommodates installation of the reference electrode 10 through the wall of an enclosure containing an aqueous system in which measurements are to made.

Referring to FIG. 2, housing 11 has a bore 22 substantially radial to the axis of housing 11 formed through oppositely facing sidewall means 19, for example by diamond tool drilling. Next referring to FIG. 3, a rod 25 preferably of the same ceramic as housing 11 is configured to mate with bore 22 to form a frictional bond when inserted therein. Rod 25 is positioned within bore 22 to extend therethrough. Rod 25 fits tightly within bore 22, and can be worked into place by twisting while urging the rod into the bore. As a result, rod 25 is held in place in bore 22 by a frictional bond from the mechanical interlocking of surface asperities on rod 25 and bore 22. Optionally, rod 25 can be further secured in place by wrapping a wire (not shown) around the ends of rod 25 and housing 11, and twisting the wire ends together to draw the wire tightly thereover.

An annular junction 28 is formed by the space remaining between rod 25 and bore 22 that provides for a transfer of ions between channel 20 and the fluid the electrode is immersed in. When the reference electrode is immersed in high-pressure water the force exerted on the ends of rod 25 balance. The high-pressure differentials that can be found across the annular junction 28 when electrode 10 is immersed in high-pressure water are balanced by the symmetrical construction of the reference electrode of this invention, so that rod 25 remains in the bore maintaining annular junction 28. As a result, a suitable annular junction is formed for stable operation of the reference electrode, without the need for forming the porous sintered annular junction shown in U.S. Pat. Nos. 4,576,667, and 4,500,413.

What is claimed is:

1. A reference electrode comprising:
   a ceramic housing comprised of a bottom and sidewall means extending therefrom to a cylindrical housing top to define an inner channel, the channel containing a silver electrode extending therefrom and a deposit of a silver salt on the silver electrode, the housing having a bore substantially radial to the axis of the housing extending through oppositely facing sidewall means, a ceramic rod configured to fit in the bore and form a friction bond is positioned in the bore to form annular junctions that permit transfer of ions across the junction, and means for electrically isolating the silver electrode mounted on the housing top.

2. An apparatus according to claim 1 wherein the electrode is spaced from the bottom leaving a channel void space, and the bore extends through a section of the sidewall means facing the void space.

* * * * *